United States Patent [19]

Kormos et al.

[11] Patent Number: 5,309,913
[45] Date of Patent: May 10, 1994

[54] FRAMELESS STEREOTAXY SYSTEM

[75] Inventors: Donald W. Kormos, Parma; Gene H. Barnett, Shaker Heights; Charles P. Steiner, Euclid, all of Ohio

[73] Assignee: The Cleveland Clinic Foundation, Cleveland, Ohio

[21] Appl. No.: 983,390

[22] Filed: Nov. 30, 1992

[51] Int. Cl.⁵ .............................................. A61B 6/00
[52] U.S. Cl. .................... 128/653.1; 606/130
[58] Field of Search ............ 128/653.1, 653.2, 660.03; 606/130; 378/4, 20, 205

[56] References Cited

U.S. PATENT DOCUMENTS

| | | | |
|---|---|---|---|
| 4,722,056 | 1/1988 | Roberts et al. | 364/413 |
| 4,793,355 | 12/1988 | Crum et al. | 128/653.1 |
| 4,896,673 | 1/1990 | Rose et al. | 128/24 EL |
| 5,230,338 | 7/1993 | Allen et al. | 128/653.1 |

OTHER PUBLICATIONS

"A Computer-Assisted System for 3-D Frameless Localization in Stereotaxic MRI" Clarysse, et al. IEEE Transactions on Medical Imaging, vol 10, No. 4, Dec. 1991.
"A Frameless, Armless Navigational System for Computer-Assisted Neurosurgery", Kato, et al. J. Neurosurg 74:845-849, May, 1991.
"A Frameless Stereotaxic Operating Microscope for Neurosurgery" Friets, et al. IEEE Transactions on Biomedical Engineering, vol. 36, No. 6, Jun. 1989.
"Reference-Display System for the Integration of CT Scanning and the Operating Microscope", Hatch, Thesis for Master of Engineering, Dartmouth College, 1984.
Cass Computer Assisted Sterotactic Surgery, MIDCO Medical Instrumentation and Diagnostics Corporation, advertising brochure, 1992.

Primary Examiner—Ruth S. Smith
Attorney, Agent, or Firm—Fay, Sharpe, Beall, Fagan, Minnich & McKee

[57] ABSTRACT

A patient's head is anchored (16) at one end of a patient support (10). An array of receivers (50) are mounted on a frame (12) which is fixed to the patient support. The frame carries at least one reference transmitter (52). A wand (42) has at least two emitters (44, 46) mounted thereto. By measuring relative travel time of the signals from the wand emitters to the receiver array and comparing the travel time with travel time over a known distance from the reference transmitter to one or more of the receivers, the position of the wand in a coordinate system of the patient support is determined (80). A three-dimensional array of diagnostic image data was taken through the anchored portion of the patient and at least three markers (114) affixed to the patient. By positioning the wand on the markers after the patient is secured to the patient support, a transform (110) between the patient support coordinate system and the image data coordinate system is derived. Once the relationship between the coordinate systems is known, the surgeon can use the wand to select locations and orientations on a surface of the patient and retrieve corresponding portions of the image data for display on video monitors (30).

19 Claims, 8 Drawing Sheets

FRAMELESS STEREOTAXY SYSTEM

BACKGROUND OF THE INVENTION

The present invention relates to the medical diagnostic and surgical arts. It finds particular application in conjunction with neurosurgery and will be described with particular reference thereto. However, it is to be appreciated, that the invention will also find application in conjunction with other medical procedures, industrial quality control procedures, and the like.

Three-dimensional diagnostic image data of the brain and other body portions are commonly available with CT scanners, magnetic resonance imagers, and other medical diagnostic equipment. These imaging modalities provide structural detail with a resolution of a millimeter or better.

Various stereotaxy procedures have been developed which require extreme accuracy. Typical neurosurgical procedures included guided-needle biopsies, shunt placements, craniotomies for lesion or tumor resection, and the like. A three-dimensional "localizer" is attached to the patient's skull. The localizer is a mechanical device with precisely known geometry and dimensions for guiding or positioning surgical instruments. The localizer is commonly attached to a ring or frame of metal or plastic from which the name "framed" stereotaxy has evolved. This frame is typically affixed to the patient using various mounting hardware methods that include sharp points or pins that pierce the skin and locate into the skull. The localizer is then mounted onto a frame. The localizer and frame provide the surgeon with the ability to position surgical instruments mechanically with a mechanical accuracy of a millimeter or better. However, anatomically, accuracy is somewhat less due to inaccuracies in the diagnostic imaging and patient motion.

One of the difficulties that has arisen is accurately coordinating the coordinate system of the patient's skull or stereotaxy localizer with the coordinate system of the diagnostic data. One solution has been to image the patient with the stereotaxic frame attached. Because the stereotaxic frame appears in the resultant images, the surgeon is provided with a frame of reference in the images. Although relatively accurate in coordinating the two frames of reference, the use of the frame has numerous drawbacks including the need to mount the frame to the patient's head for both the imaging and the surgical procedures and the associated cost.

The present invention provides a new and improved technique which simply and painlessly coordinates the coordinate system of three-dimensional image data obtained from one or more imaging modalities with the coordinate system of the patient prior to or during surgery.

SUMMARY OF THE INVENTION

In accordance with one aspect of the present invention, three or more markers are mounted to the patient's skull prior to a medical diagnostic imaging procedure. The markers contain a material which causes them to become identifiable marks in the collected medical diagnostic image. In the operating room, the patient's skull is mounted in a fixed position. The coordinates of the three markers in a coordinate system of the operating room are determined. The coordinates of the markers in the operating room and the coordinates of the markers in the three-dimensional diagnostic data are correlated. Thereafter, the surgeon denotes locations and/or directions in the coordinate system of the operating room and the corresponding image representations are retrieved from the diagnostic data for display.

In accordance with a more limited aspect of the present invention, points in the operating room coordinate system are designated through the use of a wand. The wand includes at least two emitters which emit signals on command. The signals are received by at least three receivers which triangulate or otherwise measure the location of each emitter. From a predetermined relationship between the emitters and the structure of the wand, the location and/or trajectory designated by the wand are determined.

In accordance with another more limited aspect of the present invention, a display is provided of various internal slices of the head, such as the axial, coronal, sagittal, or oblique planes through the point designated by the wand as well as a surface rendering is provided.

In accordance with another more limited aspect of the present invention, the emitters are sonic emitters. Reference emitters are provided at fixed, known distances from the receivers. The reference emitters periodically emit sonic signals, which are received by the receivers. Using the known distance from the reference emitters to the receivers, the speed of sound is recalculated to correct for temperature, humidity, air composition, etc. induced variations affecting the speed of sound.

One advantage of the present invention is that it provides a precise and accurate correlation between the reference systems of the diagnostic image data and the patient.

Another advantage of the present invention is that no frame is needed during the image acquisition scan.

Another advantage is that sterilization of necessary parts of the system is facilitated.

Another advantage of the present invention is that it is easy to use and very user friendly.

Still further advantages of the present invention will become apparent to those of ordinary skill in the art upon reading and understanding the following detailed description of the preferred embodiments.

BRIEF DESCRIPTION OF THE DRAWINGS

The invention may take form in various steps and arrangements of steps and in various components and arrangements of components. The drawings are only for purposes of illustrating the preferred embodiments and are not to be construed as limiting the invention.

DETAILED DESCRIPTION OF THE PREFERRED EMBODIMENTS

Figure 1A:
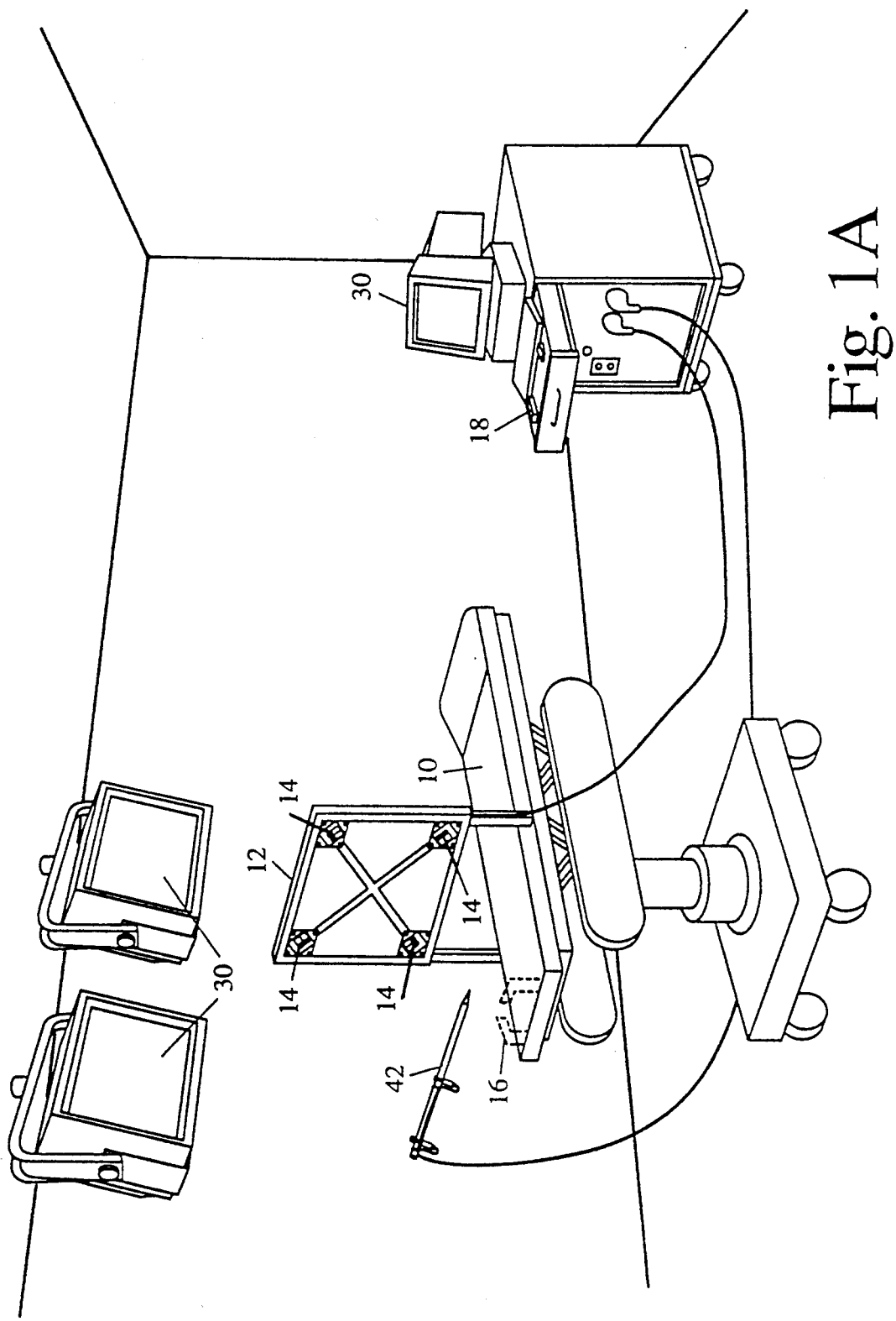
FIG. 1A is a perspective view of an operating room in which the present invention is deployed.

With reference to FIG. 1A, a subject, such as a human patient, is received on an operating table or other subject support 10 and appropriately positioned within the operating room. A frame 12 is fixed to the patient support such that it is precisely positioned within the subject or subject support coordinate system. Mounting the frame 12 to the patient support permits the patient support to be turned, raised, lowered, wheeled to another location, or the like, without altering the patient coordinate system. The frame 12 supports a plurality of emitter/receiver combinations 14 mounted at fixed, known locations thereon. Preferably, a head clamp 16 or other means securely positions the patient's head or other portion of the subject under consideration in the subject support coordinate system. The frame is mounted at a fixed or selectable angle from vertical such that the frame is positionable more toward the patient, yet still focusing on the region of interest of the patient.

Figure 1B:
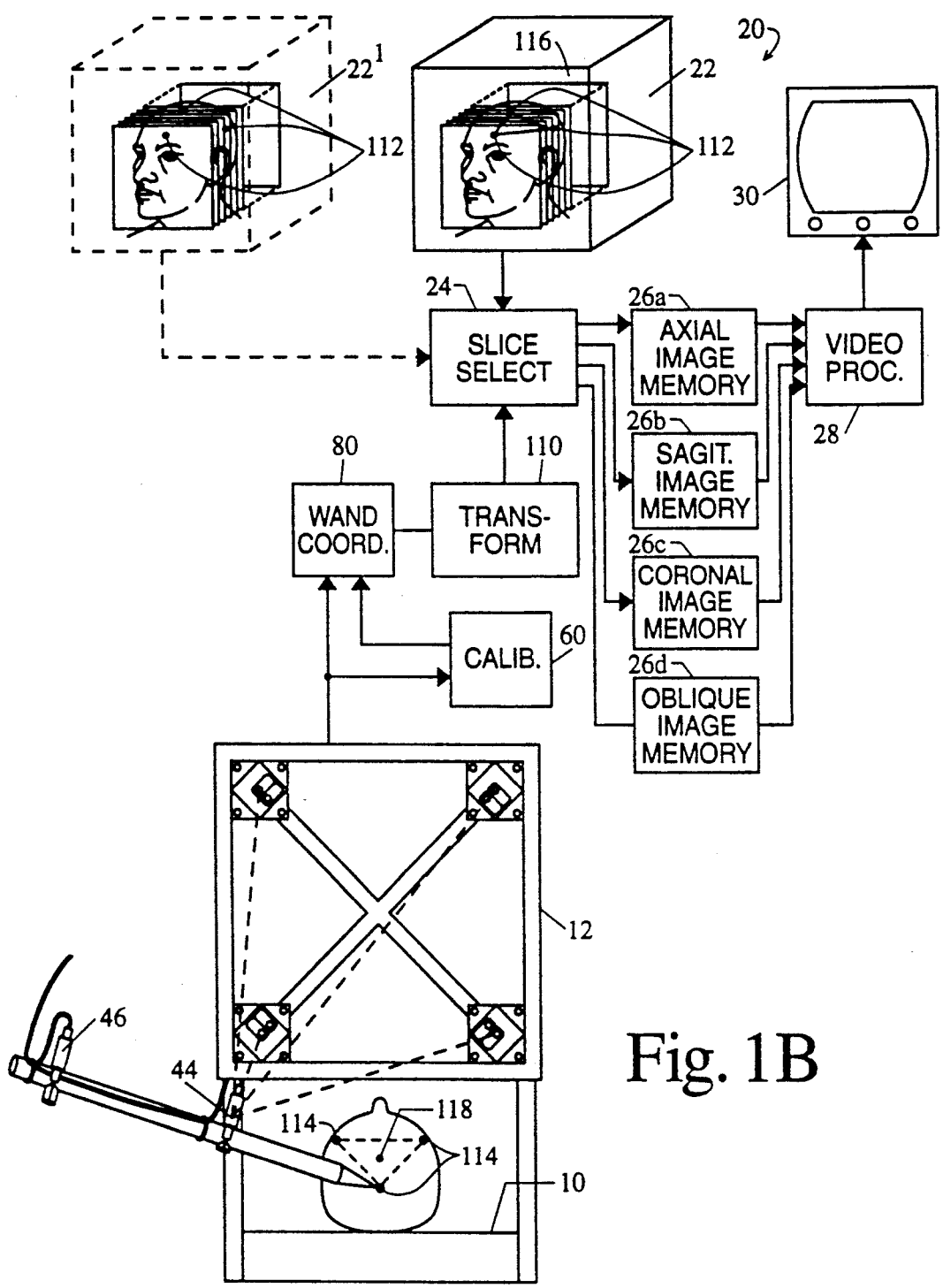
FIG. 1B is a block diagram of the image data manipulation of the system of FIG. 1A.

With continuing reference to FIG. 1A and further reference to FIG. 1B, an operator console 18 houses a computer system 20. Alternately, the computer system can be remotely located and connected with the control console 18 by cabling. The computer system includes a three-dimensional data memory 22. The stored three-dimensional image data preferably contains a video pixel value for each voxel or point in a three-dimensional rectangular grid of points, preferably a 256×256×256 grid. When each image value represents one millimeter cube, the image data represents about a 25.6 centimeter cube through the patient with one millimeter resolution. Because the data is in a three-dimensional rectangular grid, selectable orthogonal and other oblique planes of the data can readily be withdrawn from the three-dimensional memory using conventional technology. A plane selecting computer routine 24 selects various two-dimensional planes of pixel values from the three-dimensional memory for display.

In the preferred embodiment, the plane selecting computer routine selects at least four planes: axial, sagittal, coronal, and oblique planes through a selectable point of the patient. The pixel values which lie on the selected axial, sagittal, coronal, and oblique planes are copied into corresponding image memories 26a, 26b, 26c, and 26d. A video processor 28 converts the two-dimensional digital image representations from one or more of image memories 26 into appropriate signals for display on video monitors 30 or other appropriate display means.

Figure 2A:
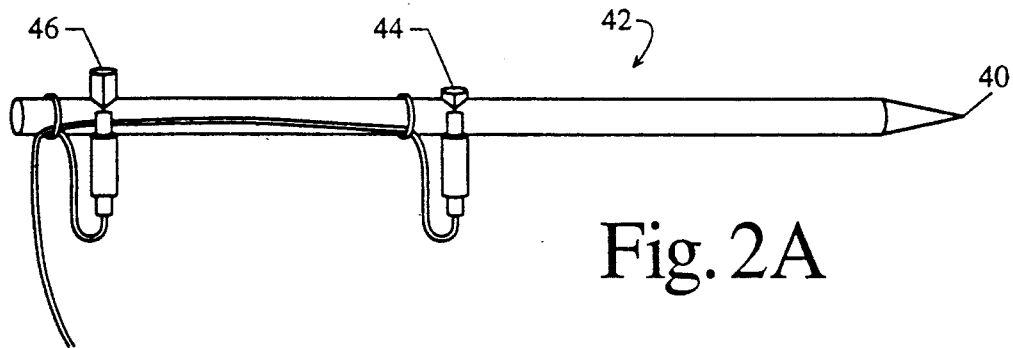
FIGS. 2A, 2B and 2C illustrate the wand of FIGS. 1A and 1B.
Figure 2B:
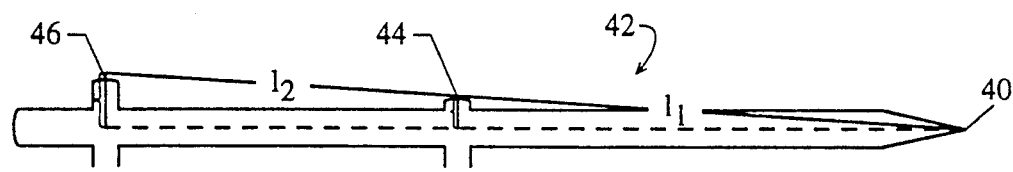
Figure 2C:
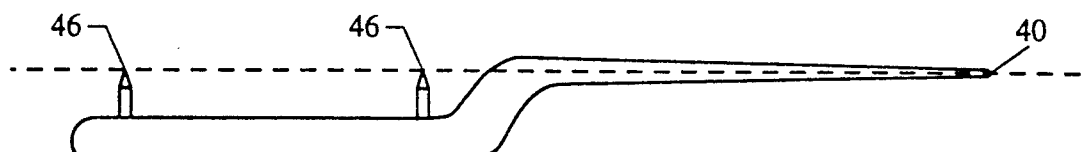

With continuing reference to FIG. 1A and further reference to FIG. 2A, in order to designate a position on the patient, the surgeon positions a tip 40 of a wand 42 at the desired location. The locator system locates the coordinate of the tip and the trajectory of the wand. More specifically, the wand includes a pair of emitters 44 and 46 which selectively emit positioning signals, ultrasonic signals in the preferred embodiment. With reference to FIG. 2B, the first emitter 44 has a fixed, known distance $l_1$ from the tip 40 and the second emitter 65 has a fixed, known distance $l_2$ from the first emitter 44. The wand is readily sterilized by conventional techniques. For simplicity of mathematical calculation, the two emitters and the tip are preferably in linear alignment. Optionally, as illustrated in FIG. 2C, the wand 42 may have a jog 48 which enables the tip and the two emitters to be disposed along a central axis or pointing direction of the wand.

Figure 3:
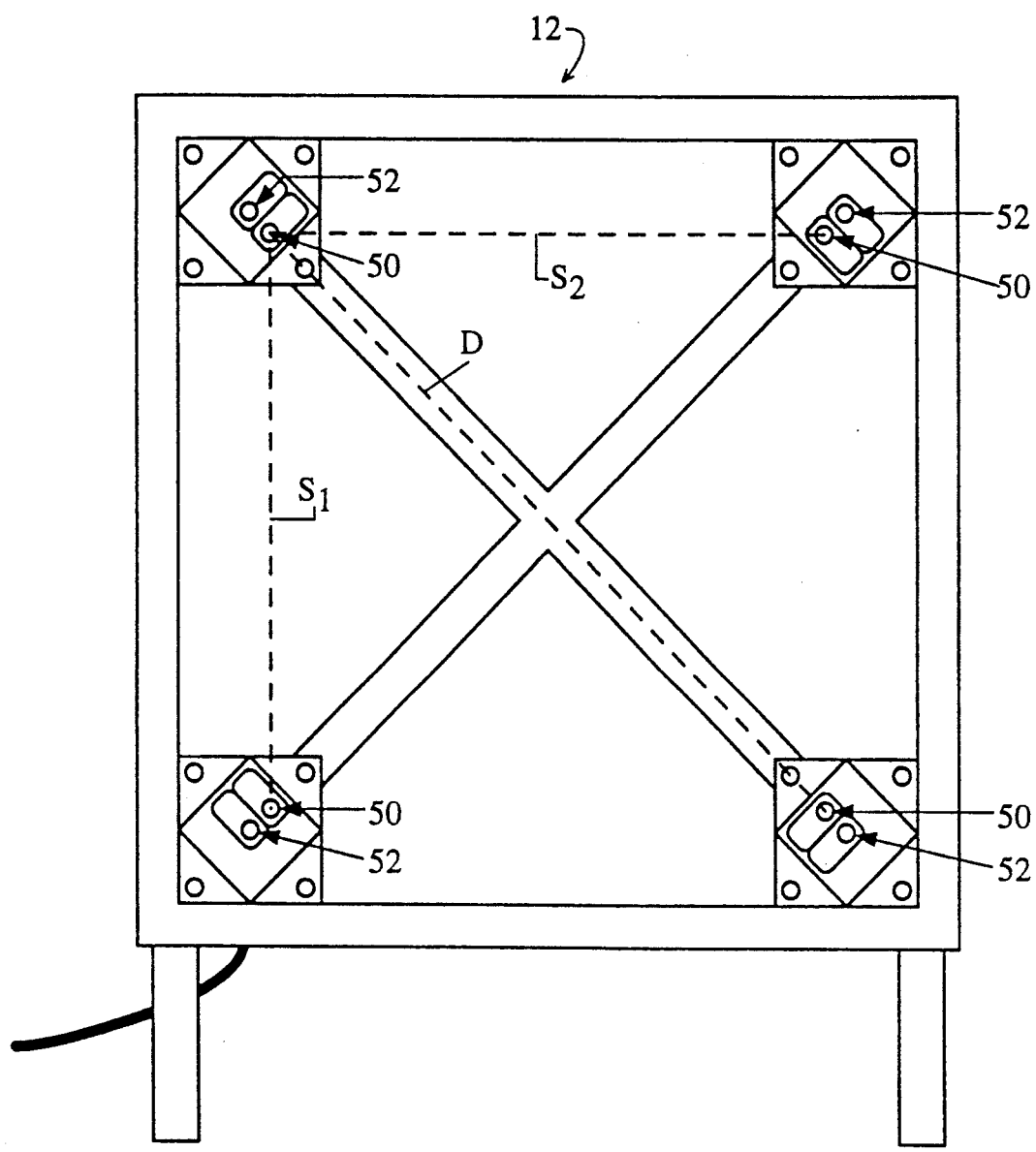
FIG. 3 is a detailed illustration of the locator assembly of FIG. 1.

With reference to FIG. 3, the frame 12 includes not only the plurality of receivers, e.g. microphones 50 in the preferred ultrasonic embodiment, but also a plurality of reference emitters 52. The reference receivers are each spaced along side edges of the frame from adjacent receivers or microphones 50 by distances $S_1$ and $S_2$. Preferably $S_1 = S_2 = S$. Each reference receiver is also spaced by a distance D across the frame from an oppositely disposed emitter 52. The emitters and the microphones are normally not coplanar with the frame 12. Preferably, both distances or range values D are equal in length.

Figure 4:
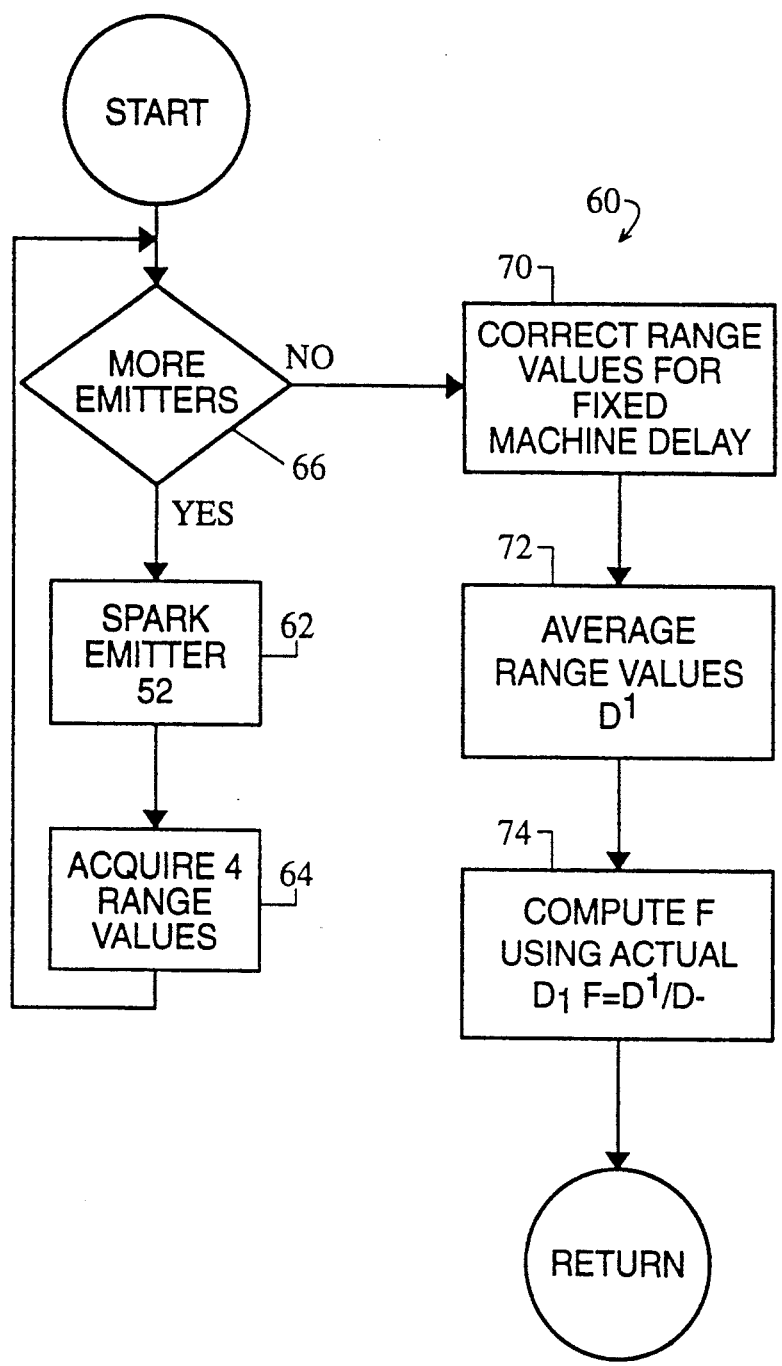
FIG. 4 is a diagrammatic illustration of one embodiment of calibration procedure in accordance with the present invention.

In the preferred embodiment, the distance from the wand emitters to the frame, hence the position of the wand relative to the patient, is determined by the travel time of the sound. The velocity of the sound pulse through air is dependent upon both the temperature, the humidity, and the chemical composition of the air. These factors can and do vary significantly during an operation and from procedure to procedure. As shown in FIG. 4, a calculation is performed to determine the speed of sound in the operating room. More specifically, a calibrating computer routine 60 selectively pulses the reference emitters 52, receives the signals at receivers 50, and processes the elapsed time information in accordance with the procedure of FIG. 4. More specifically, the calibration computer routine 60 includes a step or computer routine 62 for causing a first of the reference emitters 50 to emit a signal pulse. A step or computer routine 64 acquires the range values D', i.e. the time required for the ultrasonic pulses to traverse the distance D. A step or computer routine 66 causes this procedure to be repeated a preselected number of times, such as once for each of the four emitters illustrated in FIG. 3.

Once the travel time between each emitter and receiver pair has been obtained a preselected number of times, a step or computer routine 70 corrects the times for fixed machine delays. That is, there is a fixed, small delay between the time when the command is given to fire the reference emitters 52 and the time that they actually produce a detectable ultrasonic signal. Analogously, there is a small delay between the time that the ultrasonic pulses reach the receiver or microphone 50 and the time that it becomes a measurable electrical signal received by the computer processor. These delays are subtracted from the times measured by step or computer routine 64. An averaging computer routine 72 averages the actual times after correction for the machine delays for transmission of the ultrasonic pulse between the transmitter and receiver. The time over the range values D' provide the most accurate results. A step or computer routine 74 computes a calibration factor F indicative of the current speed of the ultrasound signal adjacent the patient in the operating room. In the preferred embodiment, the calibration factor F is a ratio of the sonically measured distance D' versus a precise mechanical measurement of the distance D.

Figure 5B:
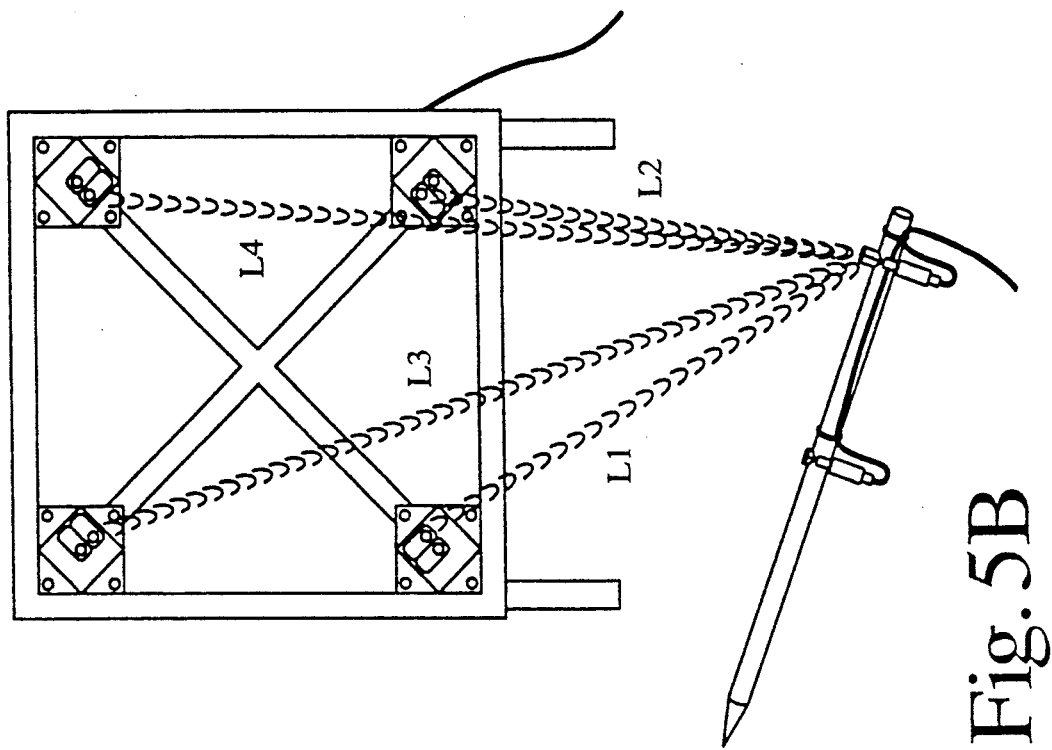
FIGS. 5A and 5B are diagrammatic illustrations of the wand and locator relationship.
Figure 5A:
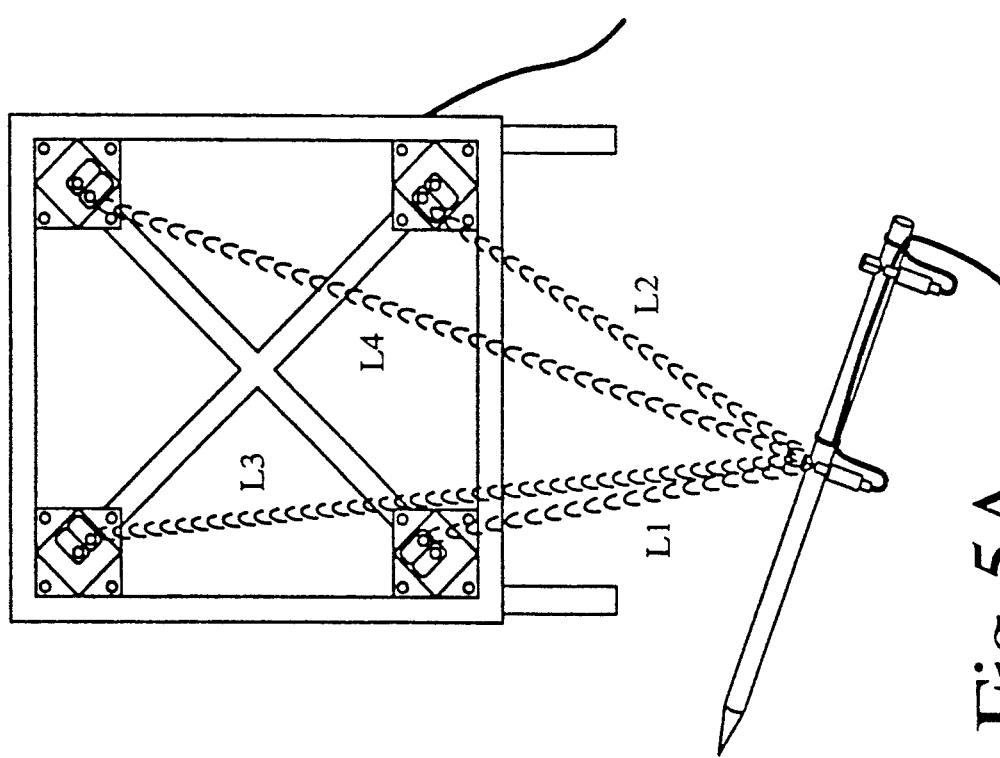
Figure 5C:
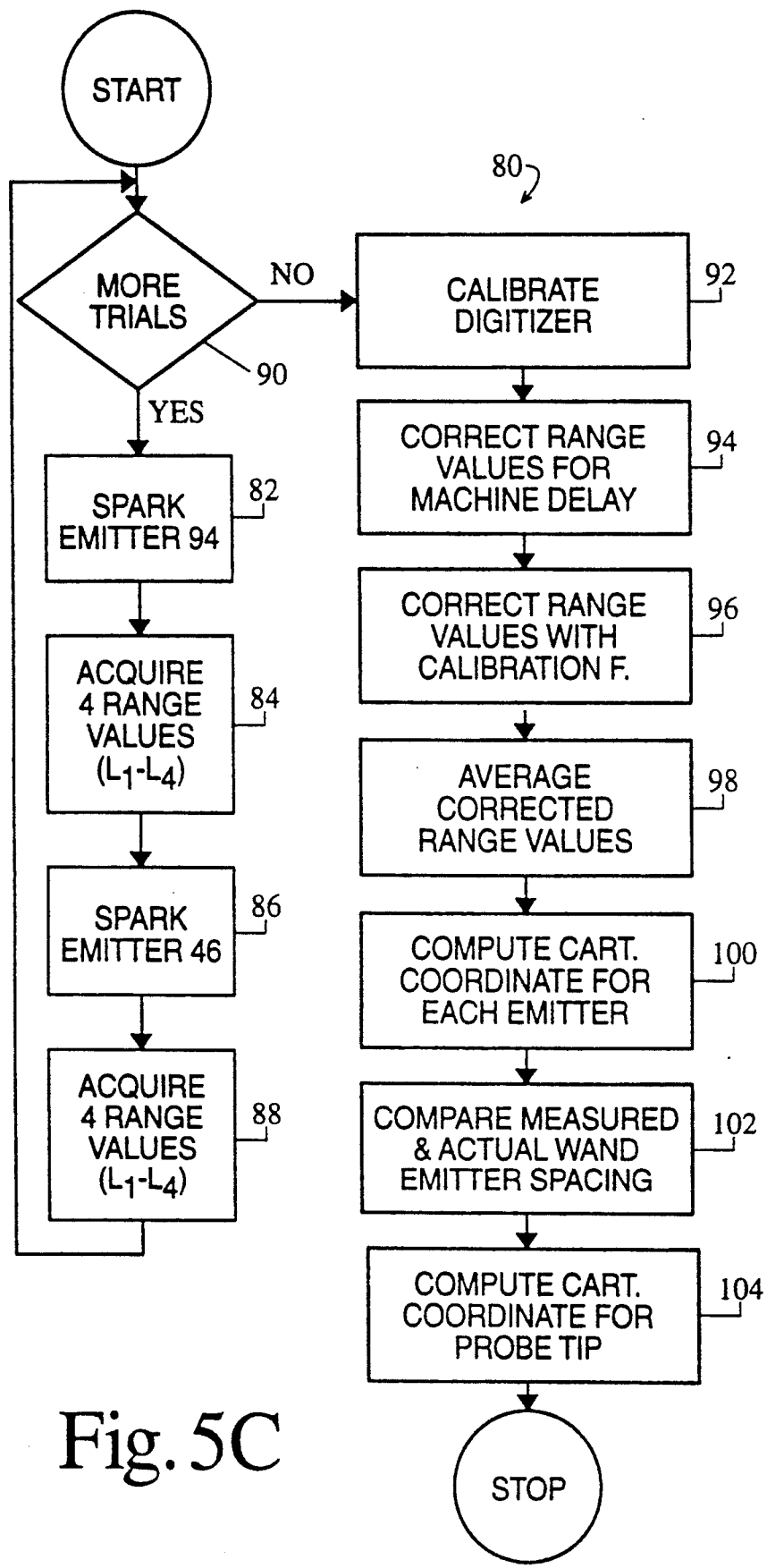
FIG. 5C is a flow diagram of the wand location procedure.

With reference to FIGS. 5A, 5B, and 5C, a wand coordinate and trajectory determining computer routine 80 determines the position of the two emitters 44 and 46, respectively. More specifically, a step or computer routine 82 causes the emitter 44 to emit an ultrasonic signal. The receivers 50 on the frame 12 receive the ultrasonic signal at corresponding times $L_1$-$L_4$. A step or computer routine 84 acquires and retains these times. A step or computer routine 86 causes the second emitter 46 to transmit. A step or means 88 acquires the four times $L_1$-$L_4$ which are required for the ultrasonic signals to pass from the second emitter to the microphones 50. The speed of ultrasonic transmission and accuracy of transmission times are such that these distances can be measured to within a millimeter or better. A step or computer routine 90 causes the emitters to emit and corresponding data values $L_1$-$L_4$ to be acquired each of a plurality of times to improve digitation accuracy, e.g. two times.

A step or computer routine 92 causes the calibration computer routine 60 to perform the steps described in conjunction with FIG. 4 in order to provide a current indication of the velocity of sound adjacent the patient. Of course, the calibration procedure of FIG. 4 may be performed immediately before steps 82–88 or intermittently during the collection of several data values for averaging. A step or computer routine 94 corrects the values $L_1$-$L_2$ for the fixed machine delay discussed above in conjunction with step or computer routine 70. A step or computer routine 96 corrects each of the times $L_1$-$L_4$ that were required for the ultrasonic signals to travel from the first and second emitters 44, 46 to the microphones 50 in accordance with the correction factor F determined by step or computer routine 74. An averaging computer routine 98 averages the delay and calibration corrected times $L_1$-$L_4$, hence distances between each of the wand emitters 44, 46 and each of the microphones 50. From these distances, provided at least three receivers 50 are provided, a step or computer routine 100 calculates the Cartesian coordinates $(x_1,y_1,z_1)$ and $(x_2,y_2,z_2)$ in the patient space for the two emitters 44 and 46. The first emitter coordinates $x_1,y_1,z_1$ are calculated from three coordinates are calculated as follows:

$$x_1 = [(L_1^2 - L_2^2) + S^2]/2S, \quad (1a)$$

$$y_1 = [(L_1^2 - L_3^2) + S^2]/2S, \quad (1b)$$

$$z_1 = [L_1^2 - x_1^2 - y_1^2]^{\frac{1}{2}}. \quad (1c)$$

where $S=S_1=S_2$ as defined in FIG. 3. Preferably, the three selected range values are the three shortest of $L_1$-$L_4$. Similar computations are calculated for $x_2$, $y_2$, and $z_2$ coordinates of the second emitter. A step or computer routine 102 checks the validity of the measurement. More specifically, the known separation between the wand emitters is compared with the separation between the measured coordinates $x_1,y_1,z_1$ and $x_2,y_2,z_2$ of the wand emitters, i.e.:

$$|Sep_{known} - [(x_1-x_2)^2 + (y_1-y_2)^2 + (z_1-z_2)^2]^{1/2}| \leq error. \quad (2)$$

If the measured and known separation is greater than the acceptable error, e.g. 0.75 mm when measuring with a resolution of 1 mm, an erroneous measurement signal is given. The measurement is discarded and the surgeon or other user is flagged to perform the measurement process 80 again. A step or computer routine 104 from the coordinates of the two emitters 44, 46, and from the geometry of the wand discussed in FIG. 2, calculates the Cartesian coordinates $(x_0,y_0,z_0)$ for the wand tip 40.

The tip coordinates $x_0$, $y_0$, $z_0$ are defined by:

$$r = l_1/l_2, \quad (3a)$$

$$x_0 = (1 + r)x_1 - rx_2, \quad (3b)$$

$$y_0 = (1 + r)y_1 - ry_2, \quad (3c)$$

$$z_0 = (1 + r)z_1 - rz_2. \quad (3d)$$

With reference to FIG. 6, a transform computer routine 110 transforms the coordinates of patient space into the coordinate system of the image data and vice versa. More specifically, prior to the imaging, three or more fiducials or markers are affixed at three or more spaced points on the patient's head. The fiducials are visible in the imaging medium selected such that they show up as readily identifiable dots 112 in the resultant image data. In the preferred embodiment, the fiducials are markers or small beads 114 that are injected with radiation opaque and magnetic resonance excitable materials. A small dot or tattoo is made on the patient's skin and a fiducial is glued to each dot. This enables the position of the fiducials to be denoted even if the fiducials are removed in the interval between the collection of the image data and the surgical procedure. Alternately, portions of the markers can be portions of the patient's anatomy which are readily identifiable in both patient and image space, e.g. the tip of the nose. To align the images of the fiducials with the fiducial positions in patient space, the tip of the wand is placed on each fiducial or tattooed marker point. The coordinates in patient space of each fiducial are determined with the procedure described in conjunction with FIGS. 5A–5C.

Figures 6A, 6B:
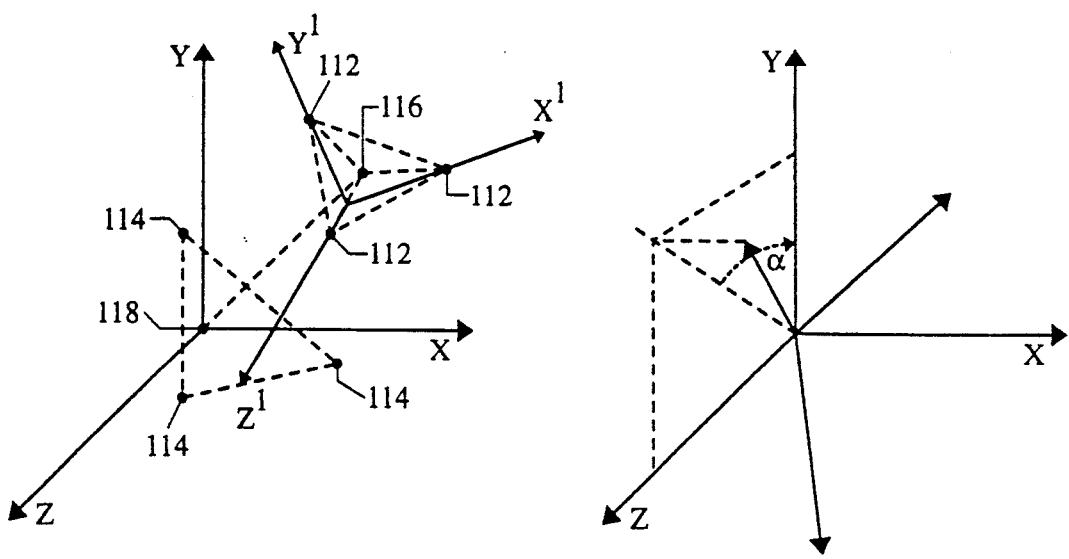
FIGS. 6A, 6B, 6C, and 6D are illustrative of a preferred coordinate transform between the coordinate system of the data and the patient.

The position of the three or more fiducials on the patient's scalp are compared with the relative position of the pixels 112 in the image space. The patient space coordinates of marks 114 on the patient's skull in the coordinate system of the patient support are measured. A like coordinate system through the pixels 112 is defined and compared to the patient space coordinate system. The translation and rotational relationship between image space and patient space coordinate systems is determined. With reference to FIG. 6A, the position of the patient in operating room space (x,y,z) and the relative position in image space (x', y',z') are determined. That is, two coordinate systems are defined. The translation computer routine first determines the offset $x_{offset}$, $y_{offset}$, $z_{offset}$ between the barycenters 116, 118 of the triangles defined by the coordinates of three fiducials in data and patient space, respectively. This provides a translation or an offset in the x, y, and z-directions between the two coordinate systems. The values of $x_{offset}$, $y_{offset}$, and $z_{offset}$ are added or subtracted to the coordinates of the patient space and the coordinates of image space, respectively, to translate between the two.

Figures 6C, 6D:
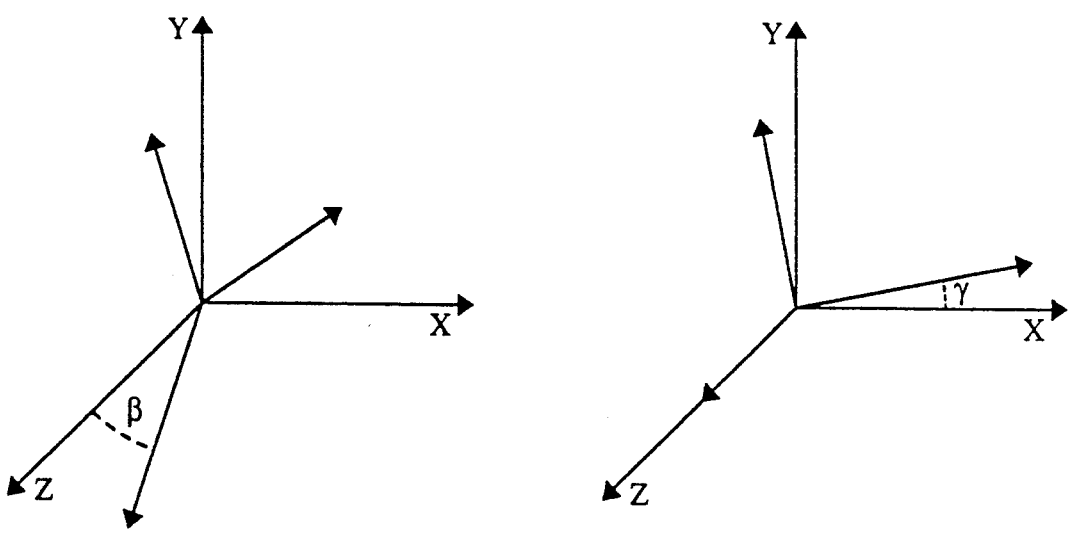

With reference to FIG. 6B, translating the origins of the two coordinate systems into alignment, however, is not the complete correction. Rather, the coordinate systems are normally also rotated relative to each other about all three axes whose origin is at the barycenter. As illustrated in FIGS. 6B, 6C, and 6D, the angle of rotation in the (y,z), (x,z), and (x,y) planes are determined. Having made these determinations, it is a simple matter to transform the patient support space coordinates into the image space coordinates and, conversely, to rotate the image space coordinates into patient space coordinates. The ward coordinate computer routine 80 is connected through the transform computer routine 110 with one of the plane selecting computer routine 24 and the video processor 28 to cause a marker, e.g. cross hairs, to be displayed on the monitors 30 at the coordinates of the wand tip. This enables the surgeon to coordinate specific points on the patient or in the incision with the images.

Having aligned the data and patient coordinate systems, numerous techniques can be performed in addition to surgery planning and verification. One can denote two locations in the patient and have them displayed on the monitor in data space. Because the measurement scale in data space is fixed, the distance between the two points is readily determined. The wand can be used to denote points on the patient and mark corresponding points in data space. The marked points can denote electrode locations for example. The present system can be used for out-patient procedures, examinations, and the like, of various parts of the patient's anatomy. Further, more than one set of diagnostic data can be coordinated with the patient. Optionally, an additional three-dimensional data memory 22' may store additional diagnostic data, e.g. from another modality, from the same modality, but at different time or with different imaging characteristics, or the like. Once both sets of diagnostic data are coordinated with the patient coordinate system, they are coordinated with each other.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A stereotaxy system comprising:
    a subject support;
    a means for securing a preselected portion of a subject to the subject support;
    a frame assembly which mounts at least three receivers in a fixed relationship to the subject support closely adjacent the means for securing a portion of the subject to the subject support;
    at least one reference emitter mounted a fixed, known distance from the receivers; the reference emitter emitting a reference signal which travels from the reference emitter the fixed distance to the receivers;
    a calibration means for measuring a reference travel time of the reference signal over the preselected distance and generating a corresponding calibration factor;
    a wand having a pointer and at least two emitters mounted thereto, the two wand emitters selectively emitting wand signals which are received by the at least three receivers;
    a wand position determining means for determining a position of the wand pointer by measuring wand signal travel times of the wand signals between the two wand emitters and the at least three receivers, the wand position determining means being connected with the calibration means for calibrating the wand signal travel times with the reference travel time.

2. The system as set forth in claim 1 further including:
    a three-dimensional image memory means for storing image data indicative of a three-dimensional region of the portion of the subject which is secured to the subject support;
    a plane selecting means for selecting planar slices of data from the three-dimensional image memory means;
    a display means for converting the selected slices of data from the plane selecting means into human-readable displays;
    a transform means for transforming with a wand pointer coordinate system to image data coordinate system transform a position of the wand pointer into a coordinate system of the image data stored in the three-dimensional image memory means, the transform means being connected with the plane selecting means such that the displayed images have a preselected relationship to the position of the wand pointer.

3. The system as set forth in claim 2 wherein the frame assembly is mounted directly to the subject support to be movable therewith such that movement of the subject support does not alter the subject coordinate system.

4. The system as set forth in claim 2 wherein the frame assembly is mounted to the subject support angled from a perpendicular relationship to focus on the secured subject region, even when mounted away from the secured region of the subject.

5. The system as set forth in claim 1 wherein a plurality of reference emitters are mounted to the frame in fixed relationship to the receivers.

6. The system as set forth in claim 1 wherein the wand includes a physical tip portion, a portion extending along a pointing axis of the wand, and an offset portion which is offset from the pointing axis of the wand, the wand emitters being mounted in a spaced relationship to the offset section in alignment with the pointing axis of the wand such that the wand tip and the two actuators are co-linear.

7. A stereotaxy system comprising:
    a subject support;
    a means for securing a preselected portion of a subject to the subject support;
    at least three markers adapted to be disposed on the preselected subject portion;
    a frame assembly which mounts at least three receivers in a fixed relationship to the subject support;
    at least one reference emitter mounted a fixed, known distance from the receivers, the reference emitter emitting a reference signal which travels from the reference emitter the fixed distance to the receivers;
    a calibration means for measuring a reference travel time of the reference signal over the preselected distance and generating a corresponding calibration factor;
    a wand having a pointer and at least two emitters mounted thereto, the two wand emitters selectively emitting wand signals which are received by the at least three receivers;
    a wand position determining means for determining a position of the wand pointer by measuring wand signal travel times of the wand signals between the two wand emitters and the at least three receivers, the wand position determining means being connected with the calibration means for calibrating the wand signal travel times with the reference travel time;

a three-dimensional image memory means for storing image data indicative of a three-dimensional region of the preselected subject portion and the markers in an image data coordinate system;

a plane selecting means for selecting planar slices of data from the three-dimensional image memory means;

a display means for converting the selected slices of data from the plane selecting means into human-readable displays;

a transform means for transforming a position of the wand pointer into a coordinate system of the image data stored in the three-dimensional image memory means with a wand pointer position to image data coordinate system transform, the transform means being connected with the plane selecting means such that the displayed images have a preselected relationship to the position of the wand pointer; and a transform calculating means for calculating the wand pointer to image data coordinate system transform from positions of the markers in the image data coordinate system determined by selectively placing the wand pointer on each of the markers.

8. The system as set forth in claim 7 wherein the markers contain materials which are visible in both magnetic resonance and CT imaging techniques such that the same markers can be used for both CT and magnetic resonance examinations.

9. A stereotaxy apparatus comprising:
a patient support;
a means for securing a preselected portion of a patient to the patient support;
a frame assembly which mounts at least three receivers in a fixed relationship to the patient support closely adjacent the means for securing a portion of the patient to the patient support;
a wand having a tip end and at least two emitters mounted thereto, the two wand emitters selectively emitting signals which are received by the at least three receivers;
a wand position determining means for determining a position of the wand tip in accordance with travel times of the signals between the two wand emitters and the at least three receivers; at least one reference emitter mounted a fixed, known distance from the receivers, the reference emitter emitting a reference signal which travels from the emitter the fixed distance to the receivers, a calibration means for measuring a travel time of the reference signal over the preselected distance, the wand position determining means being connected with the calibration means for correcting the wand tip position in accordance with the travel time of the reference signal over the fixed distance;
a three-dimensional memory means for storing image data indicative of a three-dimensional region of the portion of the patient which is secured to the patient support;
a slice selecting means for selecting slices of data from the three-dimensional memory means;
a display means for converting the selected slices of data into a human-readable display;
a transform means for transforming a position of the wand tip into a coordinate system of the image data stored in the three-dimensional image memory, the transform means being connected with the slice selecting means such that the displayed images have a preselected relationship to the position of the wand tip.

10. A stereotaxy method comprising:
a) securing a portion of a subject to a subject supporting surface in close proximity to at least three signal receivers that are mounted in a fixed relationship to the patient supporting surface;
b) positioning a wand to designate selected locations on the subject portion, the wand having at least two wand emitters mounted thereon for selectively emitting signals which are received by the receivers;
c) actuating the wand emitters to emit wand signals;
d) from the wand emitter signals, calculating a calculated wand emitter distance between the wand emitters in a coordinate system of the subject support;
e) comparing the calculated wand emitter distance with a physical distance between the wand emitters;
f) in response to the comparison of step e) exceeding a preselected standard, providing an error signal.

11. A stereotaxy method comprising:
a) securing a portion of a subject to a subject supporting surface in close proximity to at least three signal receivers that are mounted in a fixed relationship to the patient supporting surface, a reference signal emitter fixedly mounted at a fixed, known distance from the plurality of receivers;
b) positioning a wand to designate selected locations on the subject portion, the wand having at least two wand emitters mounted thereon for selectively emitting signals which are received by the receivers;
c) actuating the wand emitters individually and the reference emitter in close temporal proximity to emit wand and reference signals;
d) measuring travel durations for the wand and reference signals to travel from each of the wand emitters to the receivers and from the reference emitter to the receivers;
e) from the travel times, calculating coordinates of the locations designated by the wand in a coordinate system of the subject support.

12. The method as set forth in claim 11 further including:
calculating a distance between the wand emitters;
comparing the calculated distance between the wand emitters with a premeasured physical distance between the emitters to verify an acceptable accuracy of the measurement.

13. The method as set forth in claim 12 further including sterilizing the wand.

14. The method as set forth in claim 12 further including repeating steps (b)–(e) with the wand in a second location to calculate coordinates of the second location and further including from the coordinates of the first and second locations, determining a distance therebetween.

15. The method as set forth in claim 12 wherein the subject support coordinate system coordinates calculating step includes:
determining travel times between the wand emitters and the plurality of receivers, the relative travel times between each emitter and the receivers being indicative of a location of each emitter;

correcting at least one of (i) the relative travel times between the wand emitters and the receivers and (ii) the determined positions of the emitters in accordance with the travel time between the reference emitter and at least one of the receivers, whereby the position of the wand is corrected for variations in signal transmission speed attributable to changes in temperature, humidity, and other conditions adjacent the subject.

16. The method as set forth in claim 15 wherein:

the two wand emitters are actuated alternately a plurality of times;

the reference emitter is actuated at least once;

the travel times are adjusted for delays between (i) actuation of the emitter and emission of the signal and between (ii) the signal reaching the receiver and being converted into an electronic timing signal;

the correcting step includes correcting the travel times between the wand emitters and the receivers in accordance with the travel time between the reference emitter and the receivers; and further including:

averaging the corrected travel times and determining coordinates for each wand emitter;

from the wand emitter coordinates calculating a coordinate of a tip portion of the wand.

17. The method as set forth in claim 12 further including:

conducting a first non-invasive diagnostic examination of the subject portion and generating three-dimensional electronic image data thereof;

storing the three-dimensional image data;

determining a transform between the a first image data coordinate system and the subject support coordinate system.

18. The method as set forth in claim 17 further including:

conducting a second non-invasive diagnostic examination of the subject portion and generating three-dimensional electronic image data thereof;

storing the second examination three-dimensional image data;

determining a transform between the second image data coordinate system and the subject support coordinate system;

determining a relationship between the first and second image data coordinate systems.

19. The method as set forth in claim 17 wherein the transform determining step includes:

mounting at least three non-invasive examination visible markers to the subject portion such that the three-dimensional diagnostic image data includes indications of the at least three markers;

with the wand designating a position of each of the three markers and determining a coordinate of each marker in the subject support coordinate system;

comparing the coordinates of the markers in the subject support coordinate system and a position of the marker indications in the image data coordinate system to determine at least a translation offset between the image data and subject support coordinate systems and a rotational offset between the subject support and image data coordinate systems.

* * * * *